United States Patent [19]

Miller

[11] Patent Number: 5,074,288

[45] Date of Patent: * Dec. 24, 1991

[54] SOFT BODY BRACE

[76] Inventor: Marion E. Miller, Seaquay Condominiums, 4800 N. A-1-A, Unit 418, Vero Beach, Fla. 32963

[*] Notice: The portion of the term of this patent subsequent to Dec. 17, 2008 has been disclaimed.

[21] Appl. No.: 508,199

[22] Filed: Apr. 11, 1990

[51] Int. Cl.⁵ .................................................. A61F 5/02
[52] U.S. Cl. ........................................ 128/78; 128/85; 128/87 R; 128/869
[58] Field of Search ............... 128/78, 89 R, 90, 87 R, 128/869, 874, 95.1, 96.1, 80 R, 83, 85, 99.1, 870, 878, 882; 2/44, 92

[56] References Cited

U.S. PATENT DOCUMENTS 2,655,916 10/1953 Timmins .......................... 128/87 R
3,871,367 3/1975 Miller .................................. 128/78
4,022,197 5/1977 Castiglia ........................... 128/78 X
4,688,558 8/1987 Hooper et al. ....................... 128/78

FOREIGN PATENT DOCUMENTS 0099783 2/1984 European Pat. Off. ............. 128/78

OTHER PUBLICATIONS

Journal of Bone & Joint Surgery, British vol. 50-B, No. 2, May 1968, ZIMFOAM dressing advertisement.

Primary Examiner—Robert Bahr
Assistant Examiner—J. Doyle
Attorney, Agent, or Firm—Irving M. Kriegsman; Edward M. Kriegsman

[57] ABSTRACT

A soft body brace which may be used for providing support for non-structural deformities caused by muscle imbalance and weakness comprises an outer layer of soft compressible plastic material and an inner layer of soft compressible plastic material, the inner layer being bonded to the outer layer of soft compressible plastic material. The inner and outer layers together define a shell sized and configured to circumscribe the truck of a person and having a top edge and a bottom edge, a posterior portion and a vertically split anterior portion. A plurality of transversely spaced vertically disposed reinforcing stays are fixedly sandwiched between the outer and inner layers for maintaining the shell in the desired shape. Curved pads are also sandwiched between the inner and outer layers for engaging the iliac crests of the wearer. Releasable fasteners are attached to the open anterior ends of the shell to aid in seccuring the shell on the wearer.

7 Claims, 3 Drawing Sheets

SOFT BODY BRACE

BACKGROUND OF THE INVENTION

The present invention relates generally to a body brace and, more particularly to a soft body brace.

Body braces are well known in the art and have been used in the past for corrective and/or supportive purposes.

In U.S. Pat. No. 3,871,367 to M. E. Miller there is disclosed a body brace designed for corrective purposes comprising an outer layer of a hard substantially rigid plastic material and an inner layer of soft compressible plastic material, with the inner layer being bonded to the outer layer. The brace is shaped to engage a person's pelvis and includes an anterior portion and a vertically split posterior portion, releasable fastening means secured to the adjacent posterior portions to aid in securing the brace to a wearer and inwardly curved sections in both layers of the brace for engaging the iliac crests of the wearer, the inwardly curved sections having appreciably thicker compressible inner layers thereon. The brace is referred to in the field as the Boston Body Brace.

Another known type of body brace designed for corrective purposes comprises a shell which is sized and configured so as to circumscribe the trunk of the body and having a vertical length such as to extend at the posterior side from approximately the sacrum to approximately the eight dorsal and at the anterior side from approximately the pubic region to approximately the upper limit of the diaphragm, the shell being comprised of a flexible sheet of hard substantially rigid plastic material structured to provide a girdle having a continuous posterior side, overlapping anterior sides and lateral sides, the lateral sides containing indentations commencing at the posterior side extending forwardly therefrom and terminating at the anterior side and embodying laterally divergent portions above and below the identations dimensioned to receive, respectively, the lower part of the rib cage and the upper part of the pelvis, transversely-spaced, vertically disposed parallel stays fixed to the girdle at substantially equal distances from the ends of the overlapping anterior sides and cinches connected to the respective stays adjustable to constrain the girdle about the body. The device has become known in the field as the Boston Overlap Brace.

Both of the above described braces are classified as hard or rigid types of body braces.

The need exists for a brace for patients who need support and ease of application but cannot tolerate rigid compression as it compromises breathing or rigid three point pressure controls as it causes skin breakdown.

SUMMARY OF THIS INVENTION

The body brace of this invention is essentially for providing only support and is intended to be used, for example, by the muscular dystrophy patient whose progressive muscular atrophy leaves little strength for breathing and little tissue to cover body area, or by the severe scoliotic patient whose breathing is already compromised by a malaligned anatomy and support is indicated to relieve internal pressures, or by the insensate patient, such as the myelomeningocele, where unfelt pressure is a risk or by the cerabal palsy patient whose involuntary spasticity can be of great discomfort within a completely rigid brace.

Briefly, the body brace of this invention, which is a soft as opposed to a hard body brace in that it does not include any layers or hard material comprises a shell made up of an outer layer of a soft compressible plastic material and an inner layer of soft compressible plastic material, the inner layer being bonded to the outer layer. The brace is shaped to engage a person's pelvis and includes posterior and anterior portions, one of the portions, such as the anterior portion, being vertically split and releasable fastening means secured to the split portion to aid in securing the brace on a wearer. Inwardly curved pads may be fixedly sandwiched between the two layers of plastic material for engaging the iliac crests of the wearer. The brace further includes a plurality of reinforcing stays which are made of plastic and which are fixedly sandwiched between the layers of soft compressible plastic material for maintaining the brace in the desired shape, the stays being transversely spaced from each other and vertically oriented.

The body brace of this invention is made in the following manner. Using patient measurements taken by the orthotist or a cast supplied by the orthotist, the manufacturer selects a mold that most nearly approximates the size and shape of the patient and then alters the shape of the mold by adding plaster to it so as to conform as closely as possible to the shape of the patient. The brace is then formed on the altered mold by first pulling the inner layer, then attaching the crest pads and reinforcing stays in place on the inner layer, then pulling the outer layer and then attaching the releasable fastening means. The brace is then trimmed by the orthotist, as needed, to conform to the exact size of the wearer.

Accordingly, it is an object of this invention to provide a new and improved body brace.

It is another object of this invention to provide a new and improved method of making a body brace.

It is still another object of this invention to provide a body brace which is soft.

Various features and advantages will appear from the desription to follow. In the description, reference is made to the accompanying drawing which forms a part thereof, and in which is shown by way of illustration, a specific embodiment for practicing the invention. This embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 1:
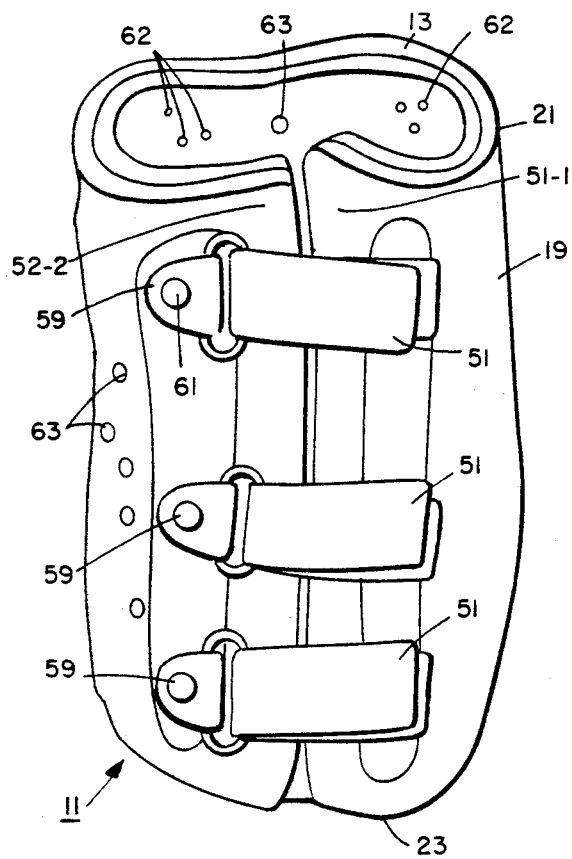
FIG. 1 is a perspective view taken from the front of a soft body brace constructed according to the teachings of the present invention.
Figure 2:
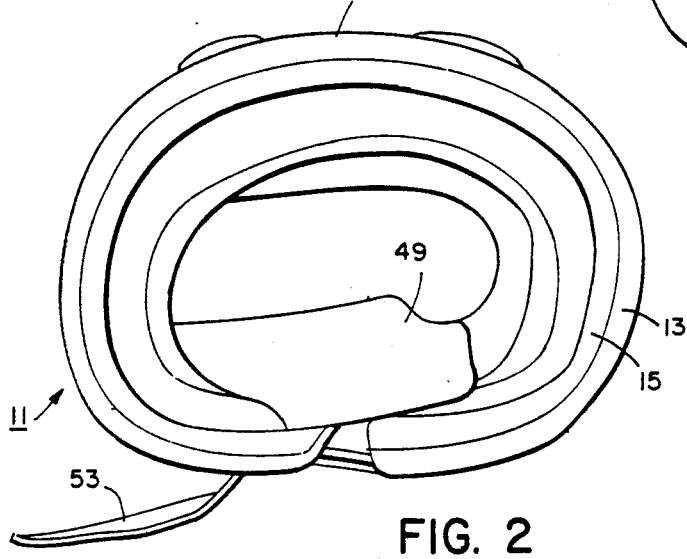
FIG. 2 is a top view of the soft body brace shown in FIG. 1.
Figure 3:
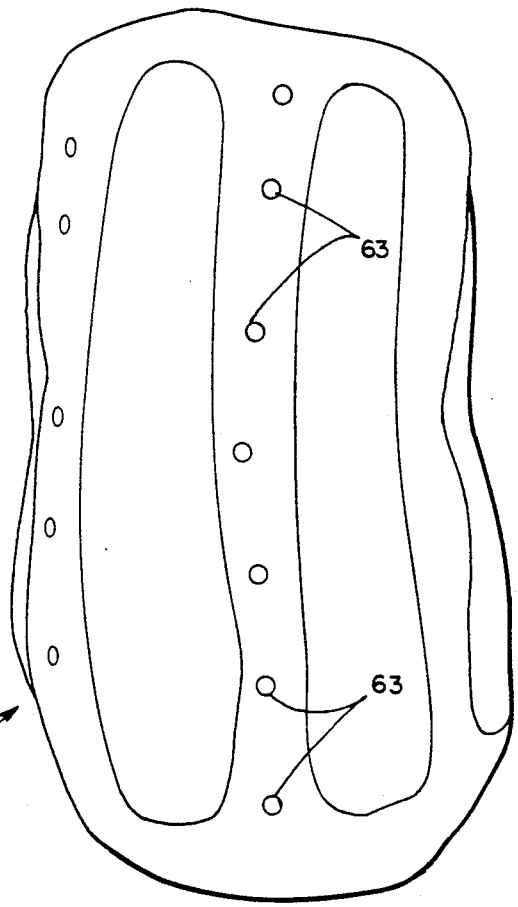
FIG. 3 is a back view of the soft body brace shown in FIG. 1.
Figures 4, 5:
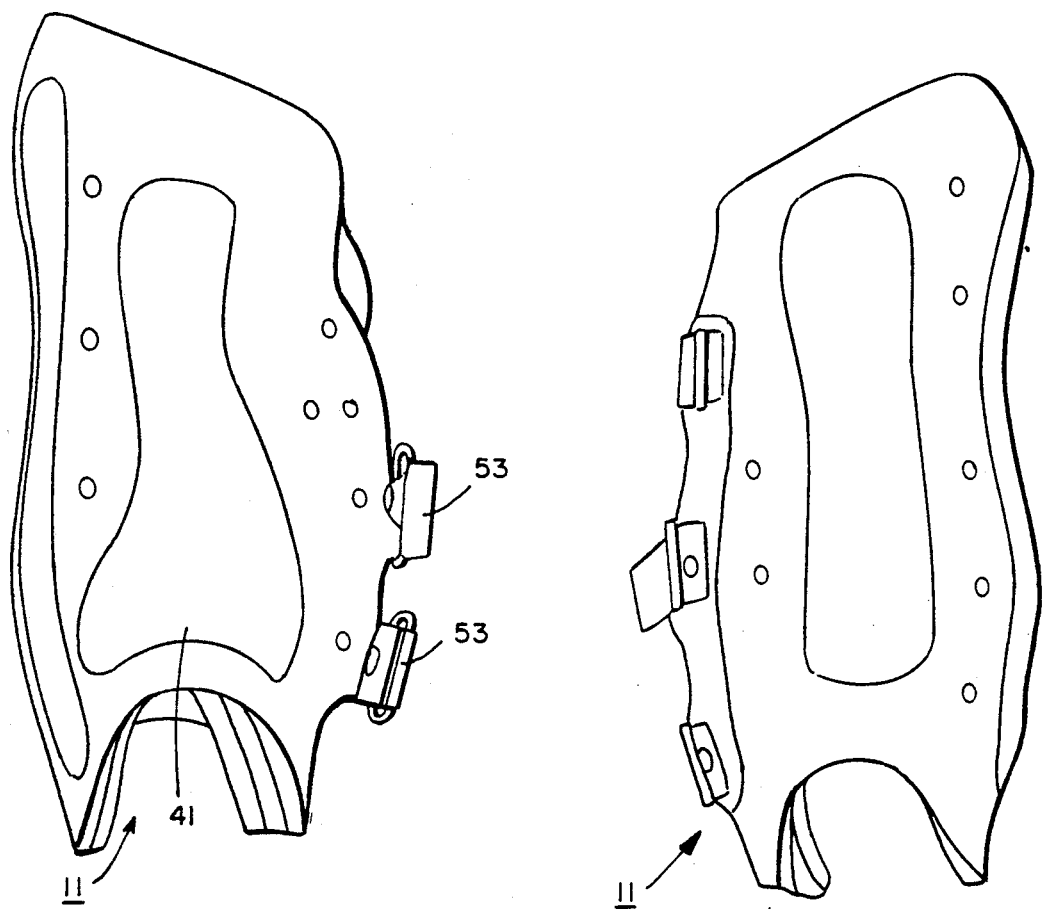
FIG. 4 is a left side view of the soft body brace shown in FIG. 1.
FIG. 5 is a right side view of the soft body brace shown in FIG. 1.

The present invention is directed to a body brace which is soft so that it can be used for example with patients who need support and ease of application but cannot tolerate rigid compression as it compromises breathing or rigid three point pressure controls as it causes skin breakdown.

Referring now to the drawings, there is shown a soft body brace constructed according to the teachings of the present invention for providing support and identified generally by reference numeral 11.

Brace 11 is sized to circumscribe the pelvic area of a person on which it is to be worn and comprises an outer layer 13 of soft compressible plastic material, such as polyethylene foam, and an inner layer 15 which is also soft compressible plastic material, such as polyethylene foam. Layers 13 and 15 are each about ¼ of an inch thick. Inner layer 15 is bonded to outer layer 13 by heat as will hereinafter be described. In addition, a suitable adhesive such as glue (not shown) may be used to enhance the bonding. Outer layer 13 and inner layer 15 define a shell 19 having a top edge 21, a bottom edge 23, a posterior portion 25, a vertically split anterior portion 27 and side portions 29 and 31.

Figure 6:
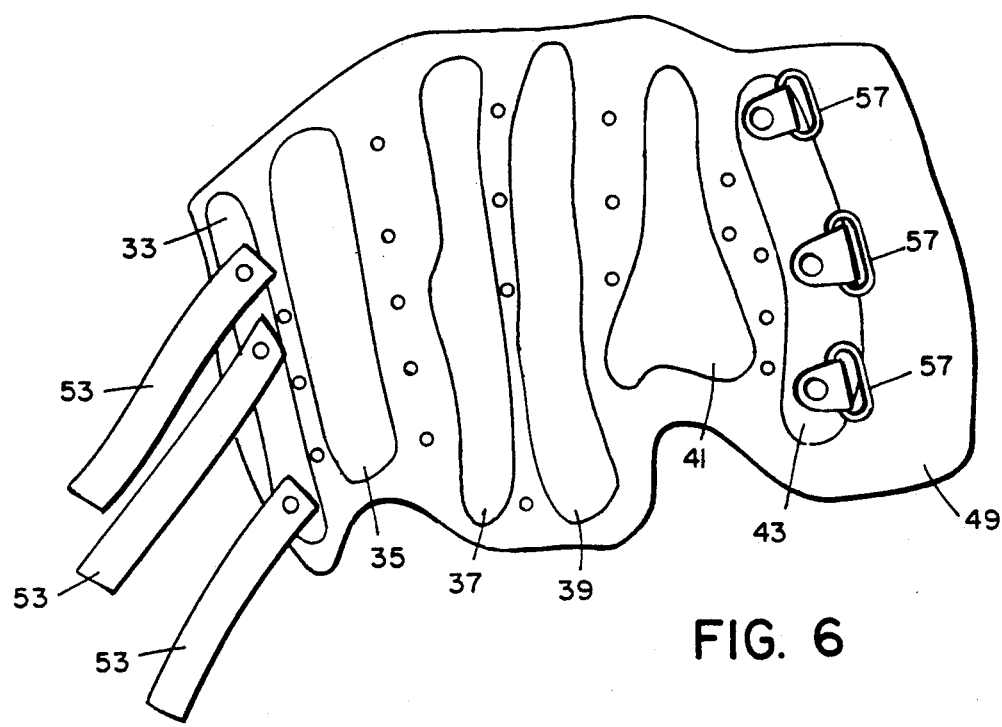
FIG. 6 is a front view of the soft body brace shown in FIG. 1, unfastened and fully opened.
Figure 7:
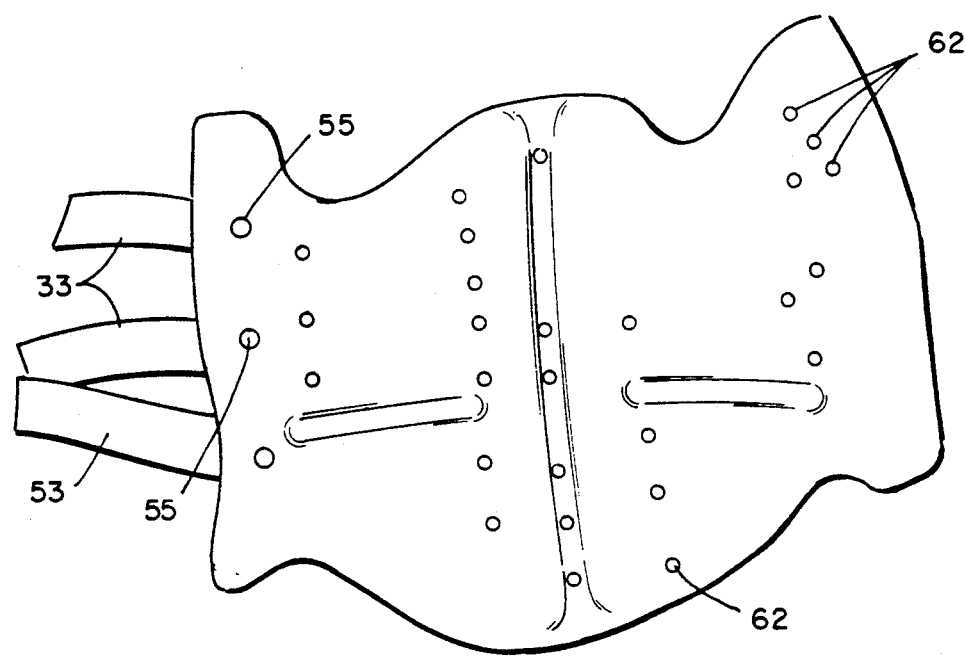
FIG. 7 is a back view of the soft body brace shown in FIG. 1, unfastened and fully opened.
Figure 8:
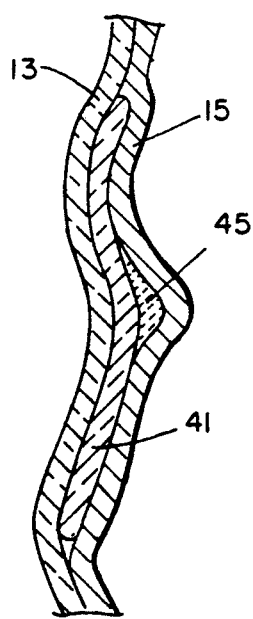
FIG. 8 is a vertical section of the left side of the soft body brace shown in FIG. 1.
Figure 9:
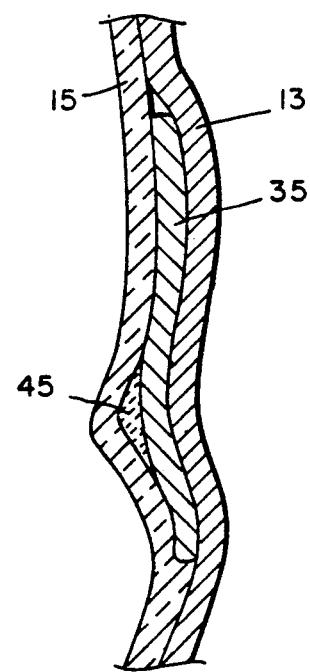
FIG. 9 is a vertical section of the right side of the soft body brace shown in FIG. 1.

A plurality of reinforcing stays 33, 35, 37, 39, 41 and 43 which are made of polyethylene or polypropyline or other suitable material which can be bonded to layers 13 and 15 by heat are fixedly sandwiched between outer layer 13 and inner layer 15 for holding brace 11 in its intended shape. Stays 33-43 are transversely oriented, vertically spaced and shaped to conform to the desired shape and contour of the brace at their respective locations. As can be seen in FIG. 1-5, there are bulges in outer layer 13 caused by the stays while in FIG. 6 the stays are shown by dotted lines.

Iliac crest pads 45 for engaging the hips of the wearer may be bonded in place between layers 13 and 15 and behind the reinforcing stays. Pads 45 may be made of soft compressible plastic material such as polyethylene foam.

A tongue 49 made of a thin sheet of soft compressible plastic material is bonded by heat to one of the anterior portions. Brace 11 is held in place on the wearer by fasteners 51. The fasteners 51 include VELCRO hook and loop pile fasteners straps 53 which are attached by rivets 55 to one anterior portion 51-1 through stay 33 and buckles 57 which are connected to the other portion 51-2 through chafes 59 which are attached by rivets 61 to stay 43.

Aeration holes 63 are formed throughout brace 11.

Soft body brace 11 may be fabricated in the following manner. First, inner layer 15 is formed by heating a first sheet of polyethylene foam or other soft compressible plastic material to a temperature such that it can be reshaped. The sheet is then wrapped around a plaster mold which is sized and shaped according to the torso of a person on which it is to be used. The plaster mold is equipped with suction (i.e. vacuum means) so that the sheet can be sucked down to conform to the shape of the mold. Plaster molds equipped with suction and used for this purpose are well known and described for example in the above noted U.S. Pat. No. 3,871,367. While the first layer is still hot, the iliac crest pads 45, which have also been heated for bonding purposes using a heat gun, are pushed down in place on the first layer. Glue may be used, if desired, to provide additional bonding. Then, stays 33-34, which have been heated so that they can be bent to a different shape and bonded in place are pressed down on the first layer so as to become bonded to the first layer and so as to conform to the shape of the first layer. Glue may be applied, if desired, to insure a good bond. Glue may then also be applied to outer surface of the shaped first layer while its still on the mold and also to the outer top side of stays 33-45. Then, a plurality of small suction holes 62 are formed throughout the first sheet. Then, a second sheet of soft compressible plastic material is heated to a temperature such that it can be shaped as desired. At the same time, the first sheet, while it is still on the mold, is heated again. The second sheet is then wrapped around the first sheet and sucked down by the vacuum to conform to the shape. The two layers are then allowed to cool.

Tongue 49 is then bonded in place using a heat gun. Removable fasteners 51 are then attached to the brace. The aeration holes 63 are then made.

The brace is then trimmed to size by the orthotist.

The embodiment of the present invention described above is intended to be merely exemplary and those skilled in the art shall be able to make numerous variations and modifications to it without departing from the spirit of the present invention. For example, other types of fasteners, such as laces which extend through holes, may be employed. Also, the split formed in the shell could be in the posterior portion rather than anterior portion or in one or both of the sides. Also, the two sheets could be attached to each other in overlapping relationship and the tongue eliminated. All such variations and modifications are intended to be without the scope of the present invention as defined in the appended claims.

What is claimed is:

1. A soft body brace for engaging the trunk of a person for supportive purposes comprising:
   a. an outer layer of soft compressible thermoplastic material,
   b. an inner layer of soft compressible thermoplastic material bonded to the outer layer of soft compressible plastic material,
   c. the inner and outer layers defining a shell having a split portion, the shell being sized and having a molded shape corresponding to the shape of the trunk of the person on whom it is to be worn, and
   d. a plurality of reinforcing stays fixedly sandwiched between the outer and inner layers to assist in holding said shell in its molded shape.

2. The brace of claim 1 and further including iliac crest pads disposed between said inner and outer layers.

3. The brace of claim 1 and wherein the stays are made of plastic.

4. The brace of claim 1 and wherein the stays are made of polyethylene.

5. The brace of claim 1 and wherein the stays are transversely spaced and vertically oriented.

6. The brace of claim 1 and wherein the inner and outer layers are made of polyethylene foam.

7. A soft body brace for engaging the trunk of a person for supportive purposes comprising:
   a. an outer layer of soft compressible plastic material,
   b. an inner layer of soft compressible plastic material bonded to the outer layer of soft compressible plastic material,
   c. the inner and outer layers defining a shell having a split portion, the shell being sized and shaped to conform to the shape of the trunk of the person on whom it is to be worn.
   d. a plurality of reinforcing stays fixedly sandwiched between the outer and inner layers to assist in holding said shell in its formed shaped, and
   e. fastening means for holding the two portions of the shell in place on the person, said fastening means comprising straps of hook and loop pile fasteners, said straps being attached to said shell through one of said stays.

* * * * *